United States Patent [19]

White et al.

[11] 4,409,218

[45] Oct. 11, 1983

[54] ANALGESIC METHOD

[75] Inventors: Alan C. White, Windsor; Gerald Bradley, Weybridge, both of England

[73] Assignee: John Wyeth and Brother Limited, Maidenhead, England

[21] Appl. No.: 357,027

[22] Filed: Mar. 11, 1982

[30] Foreign Application Priority Data

Mar. 27, 1981 [GB] United Kingdom ................ 8109713

[51] Int. Cl.³ .......................................... A61K 31/535
[52] U.S. Cl. .......................... 424/248.55; 424/248.58; 544/105
[58] Field of Search .................. 544/105; 424/248.55, 424/248.58

[56] References Cited

U.S. PATENT DOCUMENTS 3,112,311  11/1981  Zimmerman et al. ............. 544/105

Primary Examiner—Richard Raymond

Attorney, Agent, or Firm—Richard K. Jackson

[57] ABSTRACT

Morpholine derivatives of the formula

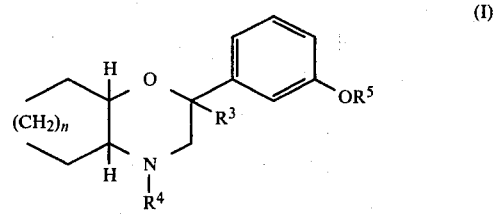

and their acid addition salts, wherein n represents 1, 2 or 3, $R^3$ is alkyl of 1 to 10 carbon atoms, $R^4$ is hydrogen, lower alkyl, lower alkenyl, lower alkynyl, aryl(lower)alkyl, 2-tetrahydrofurylmethyl or cyclo (lower)alkylmethyl and $OR^5$ is hydroxy, acyloxy or a protected hydroxy group possess analgesic and/or opiate antagonistic activity or are useful as intermediates for other compounds of formula I possessing such activity.

1 Claim, No Drawings

ANALGESIC METHOD

This invention relates to morpholines, more particularly to 2,3-trimethylene-, tetramethylene- or pentamethylene-morpholines, to processes for their preparation and to pharmaceutical compositions containing them.

The present invention provides novel morpholine derivatives of the general formula (I)

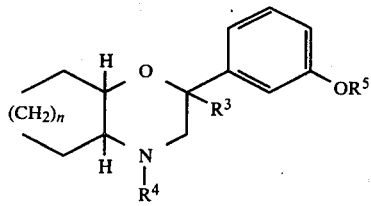

(I)

and their acid addition salts, particularly pharmaceutically acceptable acid addition salts. In this formula n represents 1,2 or 3, $R^4$ is hydrogen, lower alkyl, lower alkenyl, lower alkynyl, aryl(lower)alkyl, 2-tetrahydrofurylmethyl or cyclo(lower)alkylmethyl, $R^3$ is alkyl of 1 to 10 carbon atoms and $OR^5$ is hydroxy, acyloxy or a protected hydroxy group.

When $R^3$ is an alkyl group it is preferably a lower alkyl group. The term "lower" as used herein means that the radical referred to contains 1 to 6 carbon atoms. The radical preferably contains 1 to 4 carbon atoms. For example when $R^3$ or $R^4$ is a lower alkyl radical, the radical may be, e.g. methyl, ethyl, propyl or butyl. When $R^4$ is lower alkenyl or lower alkynyl suitable groups include, for example, allyl, 2-methyl-2-propenyl, 3-methylbut-2-enyl and propynyl. When $R^4$ is aryl(lower)alkyl the group can be, for example, benzyl or phenethyl (in which the phenyl ring may be substituted by one or more substituents such as lower alkyl, lower alkoxy, amino and halogen). When $R^4$ is cyclo(lower)alkylmethyl the group is preferably cyclopropylmethyl or cyclobutylmethyl. Preferably $R^4$ is lower alkyl. When $—OR^5$ is acyloxy the acyl group is preferably a lower alkanoyl group such as acetyl, propionyl or butyryl. When $—OR^5$ is protected hydroxy suitable groups include alkoxy (such as lower alkoxy e.g. methoxy, ethoxy, propyloxy, butyloxy particularly t-butyloxy), benzyloxy and (lower)alkoxymethoxy (e.g. methoxymethoxy) $OR^5$ is preferably hydroxy.

n is preferably 2 i.e. the preferred compounds of the invention are tetramethylenemorpholines (an alternative name for these being octahydro-2H-1,4-benzoxazines) of the general formula

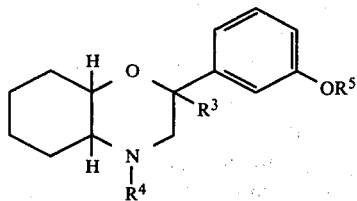

(Ia)

(where $R^3$, $R^4$ and $OR^5$ are as defined above) and their acid addition salts.

The compounds of the invention may be prepared by reduction of a lactam of general formula (II)

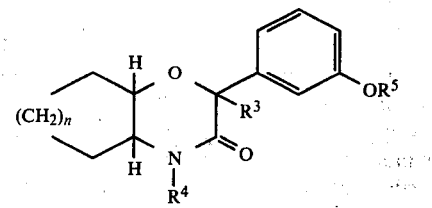

(II)

where n, $R^3$, $R^4$ and $R^5$ have the meanings given above and, if desired, converting a free base of general formula (I) into an acid addition salt thereof. The reduction may be carried out by, for example, a hydride transfer agent (e.g. lithium aluminium hydride).

Once a compound of general formula (I) has been prepared it may be converted into another compound of general formula (I) by methods known per se. For example, a compound in which $R^4$ is lower alkyl, lower alkenyl, lower alkynyl, aryl(lower)alkyl, 2-tetrahydrofurylmethyl or cycloalkylmethyl may be prepared by "N-alkylating" a compound in which $R^4$ is hydrogen. By "N-alkylating" is meant introducing on to the nitrogen atom of the morpholine ring a lower alkyl, lower alkenyl, lower alkynyl, aryl(lower)alkyl, 2-tetrahydrofurylmethyl or cycloalkylmethyl radical. In one method of carrying out the "N-alkylating" process a compound of general formula I in which $R^4$ is hydrogen is reacted with a halide of general formula $$R^{4'}\text{-Hal}$$

where $R^{4'}$ is lower alkyl, lower alkenyl, lower alkynyl, aryl(lower)alkyl, 2-tetrahydrofurylmethyl or cyclo(lower)alkylmethyl (or, is reacted with for example, a corresponding tosylate or mesylate) in the presence of an acid acceptor such as alkali metal carbonate (e.g. potassium carbonate), preferably in solution in an organic solvent.

Alternatively the compound of general formula (I) in which $R^4$ is hydrogen may be alkylated by reductive alkylation i.e. by treatment with an aldehyde and hydrogen in presence of a hydrogenation catalyst. A preferred method of cycloalkyl-methylating involves reacting the N-unsubstituted compound with a cycloalkylcarbonyl chloride to give an intermediate N-carbonyl compound which may be reduced with, for example, a hydride transfer agent.

A compound of general formula (I) in which $OR^5$ is hydroxy can be obtained by removing the protecting group from a compound in which $OR^5$ is a protected hydroxy group. For example the ether group in a compound in which $R^5$ is lower alkyl, lower alkoxymethyl or benzyl may be removed in known manner, e.g. by treating the lower alkyl or benzyl ether with hydrogen bromide or boron tribromide, by treating the lower alkyl ether with diisobutylaluminium hydride or by subjecting the benzyl ether to hydrogenolysis or by treating the (lower) alkoxymethyl or t-butyl ether with dilute acid. Similarly a compound of general formula (I) in which $R^4$ is benzyl may be hydrogenolysed to a compound of general formula (I) in which $R^4$ is hydrogen which, if desired may then be "alkylated" as hereinbefore described. Compounds in which $R^4$ is lower alkyl, particularly methyl may also be dealkylated to compounds in which $R^4$ is hydrogen, e.g. by reaction with ethyl-, phenyl-, vinyl- or 2,2,2-trichloroethyl-chloroformate followed by removal of the resulting N-substituent with, for example, dilute acid or zinc and acetic acid or basic conditions as appropriate.

A compound of general formula (I) in which OR⁵ is hydroxy can be acylated (e.g. with acetic anhydride) to give a corresponding compound in which OR⁵ is an acyloxy group such as a lower alkanoyloxy radical.

Two or more of the above mentioned processes for interconverting the compounds of general formula (I) may, if desired, be carried out consecutively. In some instances it may be necessary to protect one or more of the functional groups on the molecule while reaction occurs at another functional group and then subsequently remove the protecting group or groups.

Lactams of general formula (II) may be prepared by cyclisation of an amide of general formula

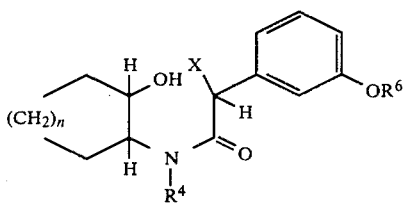

(III)

(where n and R⁴ are as defined above, X is bromo or chloro, and OR⁶ is a protected hydroxy group) and alkylation of the product. The cyclisation may be carried out with a basic agent such as an alkali metal hydride or alkali metal hydroxide. The alkylation may be carried out, for example, with an alkyl halide in presence of a strong base such as sodamide, lithium diisopropylamide, lithium tetramethylpiperidide, bromomagnesium diisopropylamide or N-tertiarybutylcyclohexylamide.

If desired, the —OR⁵ protected hydroxy group in the lactam of formula (II) may be deprotected to give a lactam where —OR⁵ is hydroxy. In this case the protecting group and the method of deprotection are chosen, for example, from those mentioned hereinabove, so that the product is stable under the chosen conditions.

The amides of formula (III) are preferably prepared by condensing an α-halo acid halide of general formula (IV)

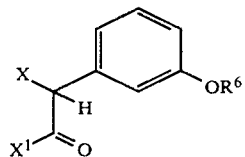

(IV)

with an amino alcohol of general formula

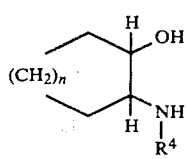

(V)

In general formula (IV) and (V) n, R⁴, OR⁶ and X have the meanings given above and X¹ is chloro or bromo.

The condensation can be carried out in presence of a basic condensing agent, eg. triethylamine.

The α-halo acid halide of general formula (IV) and the amino alcohol of general formula (V) are known compounds or can be prepared by methods known for analogous compounds. For example, the choice of method used to prepare the amino alcohol will depend upon the stereochemistry required in the final product. For example, an oxiran of formula (VI) may be reacted with an amine of formula R⁴NH₂ to give the trans-aminoalcohol of formula (VII)

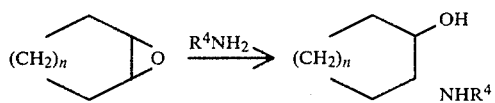

(VI)  (VII)

Methods for preparing the cis-aminoalcohols of formula (VIII)

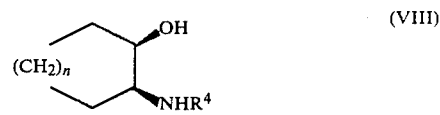

(VIII)

are known, see for example, K. B. Sharpless et al., J.Org Chem., 1976, 41, 177; J.Org. Chem., 1978, 43, 2544 and J. Org. Chem., 1980, 45, 2710.

If in any of the processes described above the compound of the invention is obtained as an acid addition salt, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromide, phosphoric, tartaric, fumaric, oxalic, maleic, citric, acetic, formic, methanesulphonic and p-toluenesulphonic acids.

The compounds of the invention contain at least three asymmetric carbon atoms and hence can exist in more than one isomeric form. For example the hydrogen atoms at the bridgehead carbon atoms may be cis or trans to each other and also the hydrogen atom at the bridgehead carbon atom may be cis or trans to the

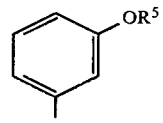

substituent. The various isomeric forms can be obtained or separated by standard procedures. For example, as exemplified above, by suitable choice of starting materials products can be obtained with the desired configuration. The products will normally be obtained as racemates of the d- and l-enantiomorphs but optical isomers may be prepared by resolving a racemic mixture by standard methods described in the literature. The racemate may be prepared by any of the processes outlined above. It is to be understood that the resolution may be carried out on the racemic mixture of the final desired product or it may be carried out on a racemic precursor of the desired compound provided further chemical transformations do not cause racemisation.

The compounds of the invention in which $OR^5$ is a protected group, such as lower alkoxy, are useful as intermediates for compounds in which $OR^5$ is hydroxy as explained above. The compounds of formula (I) in which $OR^5$ is hydroxy or acyloxy and their pharmaceutically acceptable acid addition salts possess analgesic activity and/or opiate antagonistic activity. Some compounds also possess hypotensive or antihypertensive activity. In a standard test for analgesic activity in which the compound is assessed for its ability to inhibit phenyl-benzoquinone-induced writhing in mice (based upon the method of E. Siegmund et al., Proc. Soc. exp. Biol. Med., 1957, 95, 729–731) 3-[(2R*, 4aS*, 8aS*)-2-ethyl-4-methyl-octahydro-2H-1,4-benzoxazin-2-yl]phenol, a representative compound of the invention, exhibited an $ED_{50}$ of 9.2 mg/kg (subcutaneous). In a standard test for opiate antagonism based upon the antagonism of morphine-induced Straub tail in mice (Aceto et al., Brit. J. Pharmac., 1969, 36, 225–239), the same compound exhibited an $ED_{50}$ of 23.9 mg/kg (subcutaneous).

The invention provides a pharmaceutical composition comprising a compound of general formula (I) in which $OR^5$ is hydroxy or acyloxy or a pharmaceutically acceptable acid addition salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, lactose, pectin, dextrin, starch, gelatin, tragacanth, methylcellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intra-muscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredients; the unit dosage forms can be packaged compositions, for example packeted powders or vials or ampoules. The unit dosage form can be a capsule, cachet or tablet itself, or it can be the appropriate number of any of these in package form. the quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form. The following Examples illustrate the invention.

EXAMPLE 1

(2R*,4aR*,8aR*) and (2R*,4aS*,8aS*)-2-(3-Methoxyphenyl)-4-methyl-hexahydro-2H-1,4-benzoxazin-3-(4H)-one 3-Methoxymandelic acid (crude, 10.16 g) was heated to reflux in thionyl chloride (25 cm$^3$) for ½ hr. The cooled solution was concentrated under reduced pressure and the residue was re-evaporated with toluene. The residual oil was dissolved in dichloromethane (50 cm$^3$) and added dropwise over 3 hr. at room temperature to a solution of trans-2-methylaminocyclohexanol (7.58 g) in dichloromethane (50 cm$^3$), containing triethylamine (7.8 cm$^3$). The mixture was left at room temperature overnight and was then concentrated under reduced pressure. The residual solution was diluted with an equal volume of ether, and was then extracted with 2 N hydrochloric acid (25 cm$^3$), washed with water and saturated brine, dried (Na$_2$SO$_4$) and evaporated, leaving crude trans-N-(2-hydroxycyclohexyl)-N-methyl-2-(3-methoxyphenyl)-2-chloroacetamide as an orange-brown gum (15.35 g).

The crude chloroacetamide (3.1 g) was dissolved in propan-2-ol (30 cm$^3$) and treated with 10 N sodium hydroxide solution (3 cm$^3$). The mixture was stirred at room temperature for 5 hrs. and was left overnight. The phases were separated and the organic phase was concentrated under reduced pressure. The residue was dissolved in ether-dichloromethane (1:1 v/v, 70 cm$^3$) and washed with the alkaline phase diluted with water. The aqueous phase was extracted with dichloromethane (2×30 cm$^3$). The combined organic phases were washed with saturated brine, dried (Na$_2$SO$_4$), and evaporated, leaving crude mixture of the title compounds as a brown oil (2.11 g).

EXAMPLE 2

(2R*,4aR*,8aR*) and (2R*,4aS*,8aS*)-2-Ethyl-2-(3-methoxyphenyl)-4-methyl-hexahydro-2H-1,4-benzoxazin-3-(4H)-one Impure, distilled, benzoxazinone product from Example 1 (6.86 g) in dry THF (25 cm³) was added at room temperature under nitrogen to lithium di-isopropylamide (from di-isopropylamine, 5 cm³, in dry THF, 10 cm³, and n-butyl lithium, 1.6 M in hexane, 22 cm³). The resulting solution was stirred at room temp. for 1 hr. and was then treated with bromoethane (7 cm³, 9.52 g) over 5 min. The mixture was kept at room temp. for a further 2½ hr. and was then poured into 2 N hydrochloric acid (50 cm³) and concentrated under reduced pressure. The residual aqueous phase was diluted with an equal volume of saturated brine and extracted with ether (4×50 cm³). The combined extracts were dried (Na₂SO₄) and evaporated, leaving a mixture of the crude title compounds as a brown oil (7.25 g).

EXAMPLE 3

(2R*,4aR*,8aR*)-2-Ethyl-2-(3-methoxyphenyl)-4-methyloctahydro-2H-1,4-benzoxazine, and (2R*,4aS*,8aS*)-2-ethyl-2-(3-methoxyphenyl)-4-methyloctahydro-2H-1,4-benzoxazine Crude lactam product from Example 2 (7.25 g) in ether (100 cm³) was added to a suspension of lithium aluminium hydride (0.9 g) in ether (25 cm³) and the mixture was heated to reflux for 6½ hr and allowed to cool overnight. Saturated Rochelle salt solution (50 cm³) was added and the mixture was stirred. The phases were separated and the aqueous phase was extracted with ether. The combined organic phases were evaporated leaving a mixture of the title compounds as a yellow oil.

The mixture (5.19 g) was separated by chromatography over silica.

The (2R*,4aR*,8aR*) product (1 g) was converted to its toluene-4-sulphonate salt in ethyl acetate giving colourless crystals (1.51 g) m.p. 182.5°–184°.

Found: C, 65.0; H, 7.7; N, 2.8. $C_{18}H_{27}NO_2 \cdot C_7H_8O_3S$ requires C, 65.0; H, 7.6; N, 3.0%.

The (2R*,4aS*,8aS*) product (0.5 g) was similarly converted to its toluene sulphonate salt in ethyl acetate, giving crystals, m.p. 159°–160°.

Found: C, 64.7; H, 7.9; N, 2.8. $C_{18}H_{27}NO_2C_7H_8O_3S$ requires C, 65.0; H, 7.6; N, 3.0%.

EXAMPLE 4

3-[(2R*,4aR*,8aR*)-2-Ethyl-4-methyl-octahydro-2H-1,4-benzoxazin-2-yl]phenol (2R*,4aR*,8aR*)-2-Ethyl-2-(3-methoxyphenyl)-4-methyloctahydro-2H-1,4-benzoxazine (1.74 g) in dry toluene (5 cm³) was added under nitrogen to di-isobutylaluminium hydride (20% w/w in toluene, 1.2 M, 30 cm³). The mixture was heated to reflux under nitrogen for 24 hr. The mixture was cooled in ice to 0° and treated carefully with saturated Rochelle salt solution followed by toluene (50 cm³). The phases were separated, and the aqueous phase was extracted with ether. The combined organic phases were dried (Na₂SO₄) and evaporated, leaving the title base as a slightly cloudy oil which crystallised to a colourless solid (1.65 g), m.p. 134°–8°.

This solid (1.45 g) was dissolved in ethyl acetate (30 cm³) and the warm solution was filtered into a solution of toluene-4-sulphonic acid monohydrate (1.00 g, 1 equiv) in ethyl acetate (10 cm³). Solid deposited rapidly and was digested by addition of methanol (20 cm³) to allow recrystallisation from the hot solvent, giving the title compound toluene-4-sulphonate salt as colourless crystals (1.78 g) m.p. 261°–4°.

Found: C, 64.15; H, 7.7; N, 2.95. $C_{17}H_{25}NO_2 \cdot C_7H_8O_3S$ requires C, 64.4; H, 7.4; N, 3.1%.

EXAMPLE 5

3-[(2R*,4aS*,8aS*)-2-Ethyl-4-methyloctahydro-2H-1,4-benzoxazin-2yl]phenol (2R*,4aS*,8aS*)-2-Ethyl-2-(3-methoxyphenyl)-4-methyloctahydro-2H-1,4-benzoxazine (0.5 g) in dry toluene (5 cm³) was added under nitrogen to di-isobutylaluminium hydride (20% in toluene, 1.2 M, 15 cm³) at room temperature. The mixture was then heated to reflux under nitrogen for 5¼ hr. The mixture was cooled in ice to 0° and treated cautiously with saturated Rochelle salt solution (75 cm³) and the mixture was stirred for 1 hr. Ether (30 cm³) was added and the phases were separated. The aqueous phase was then treated with an equal volume of saturated ammonium chloride solution and was extracted with further ether. The combined organic phases were dried (Na₂SO₄) and evaporated, leaving impure title compound base as a cloudy oil which crystallised to a pale yellow mass (0.45 g).

This mass (0.45 g) was dissolved in ethyl acetate and filtered into a solution of toluene-4-sulphonic acid monohydrate (0.31 g) in ethyl acetate. The solution was kept overnight to afford title compound toluene-4-sulphonate salt hemihydrate as colourless crystals (0.56 g) m.p. 234°–5°.

Found: C, 63.1; H, 7.5; N, 2.8. $C_{17}H_{25}NO_2C_7H_8O_3S \cdot \tfrac{1}{2}H_2O$ requires C, 63.1; H, 7.5; N, 3.1%.

We claim:

1. A method of treating a mammal in need of an analgesic which comprises administering to said mammal an analgesically effective amount of a 2R*,4aS*,8aS* morpholine derivative of the formula

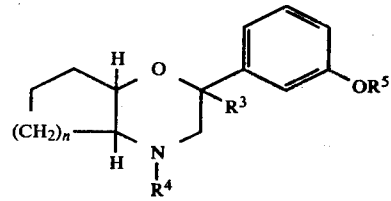

or a pharmaceutically acceptable acid addition salt thereof, wherein n represents 1, 2 or 3; $R^3$ is alkyl of 1 to 10 carbon atoms; $R^4$ is hydrogen, lower alkyl, lower alkenyl, lower alkynyl, aryl(lower)alkyl, 2-tetrahydrofurylmethyl or cyclo(lower)alkylmethyl; and $OR^5$ is hydroxy or acyloxy.

* * * * *